United States Patent
Månsson et al.

(10) Patent No.: US 11,779,753 B2
(45) Date of Patent: Oct. 10, 2023

(54) POSITIONING OF ELECTRODES FOR TRANSCRANIAL BRAIN STIMULATION

(71) Applicant: Flow Neuroscience AB, Malmö (SE)

(72) Inventors: Daniel Månsson, Simrishamn (SE); Erik Rehn, Enebyberg (SE)

(73) Assignee: FLOW NEUROSCIENCE AB, Malmö (SE)

( * ) Notice: Subject to any disclaimer, the term of this patent is extended or adjusted under 35 U.S.C. 154(b) by 91 days.

(21) Appl. No.: 17/264,308

(22) PCT Filed: Jul. 23, 2019

(86) PCT No.: PCT/EP2019/069749
§ 371 (c)(1),
(2) Date: Jan. 29, 2021

(87) PCT Pub. No.: WO2020/025388
PCT Pub. Date: Feb. 6, 2020

(65) Prior Publication Data
US 2021/0299434 A1    Sep. 30, 2021

(30) Foreign Application Priority Data
Jul. 31, 2018 (EP) .................................... 18186520

(51) Int. Cl.
*A61N 1/36* (2006.01)
*A61N 1/04* (2006.01)

(52) U.S. Cl.
CPC ......... *A61N 1/0456* (2013.01); *A61N 1/0476* (2013.01); *A61N 1/0484* (2013.01); *A61N 1/3603* (2017.08); *A61N 1/36025* (2013.01)

(58) Field of Classification Search
CPC ............................ A61N 1/0526; A61N 1/0529
See application file for complete search history.

(56) References Cited

U.S. PATENT DOCUMENTS

2015/0190635 A1*  7/2015  Neuvonen ............ A61N 1/3603
                                                                    607/139
2015/0238762 A1   8/2015  Pal et al.
2017/0224991 A1   8/2017  Wingeier et al.

FOREIGN PATENT DOCUMENTS

GB    2521877 A    7/2015
GB    2541947 A    3/2017

OTHER PUBLICATIONS

International Search Report and Written Opinion dated Oct. 9, 2019, received for PCT Application PCT/EP2019/069749, Filed on Jul. 23, 2019, 12 pages.

* cited by examiner

*Primary Examiner* — Alyssa M Alter
(74) *Attorney, Agent, or Firm* — COOLEY LLP (57) ABSTRACT

A method of guiding positioning of a headset for transcranial brain stimulation on a head of a user of the headset is disclosed The method includes: capturing, using a camera, one or more head images depicting the head; detecting, in the one or more head images, features of the head; creating, using the detected features of the head, a model of the head; computing, using the model of the head, an intended headset position on the head; and displaying, on a display, a representation of the headset as an overlay on an image of the head of the user. Also a kit includes a headset for transcranial brain stimulation, and a non-transitory computer-readable recording medium is disclosed, which configures an electronic device to perform the method of guiding positioning of a headset.

16 Claims, 5 Drawing Sheets

POSITIONING OF ELECTRODES FOR TRANSCRANIAL BRAIN STIMULATION

CROSS-REFERENCE TO RELATED APPLICATIONS

The present application is based on PCT filing PCT/EP2019/069749, filed Jul. 23, 2019, which claims priority to EP 18186520.5, filed Jul. 31, 2018, the entire contents of each are incorporated herein by reference.

TECHNICAL FIELD

The present invention relates to positioning of electrodes for transcranial brain stimulation. A method for guiding and possibly also verify positioning of electrodes for transcranial brain stimulation on a head of a user of the electrodes is presented.

BACKGROUND OF THE INVENTION

Transcranial brain stimulation is, e.g., used to help stroke recovery and patients with brain injuries and to treat depression. An example of transcranial brain stimulation is transcranial direct current stimulation, tDCS, which is a well-known technique for non-invasive neurostimulation of the brain. Transcranial brain stimulation uses external electrodes placed on the head of the patient, whereby the head of the patient together with the electrodes forms a closed circuit. A current, either direct or alternating, is applied to the circuit, which acts on the neurons of the brain.

However, there is a problem to ensure that the electrodes are positioned correctly. Positioning of the electrodes is typically made by a physician having experience in how to position a headset for transcranial brain stimulation such that the electrodes are positioned correctly. However, for some implementations of transcranial brain stimulation, e.g. to treat depression, it is highly impractical for a physician to be present at every treatment session. This since treatment is to be made on a daily basis for a period of time ranging from weeks to months. As mentioned in WO2009137683, the patient may be given the electrodes and instructions on how to place them, but this is of course error-prone. Further, according to WO 2016042499 A1 correct position a headset for transcranial brain stimulation may be secured by arranging a positioning indicator on the headset. The positioning indicator enables the user, during donning of the headset, to center the headset on the head of the user such that the at least one electrode is accurately positioned when the headset is donned. The positioning indicator is in the form of notches, or other tactilely distinguishable features, on the headset. The notches assist the user in donning the headset correctly by providing verification for headset placement, for example by helping the user confirm that the notches are aligned with the user's nose. The notches or other tactilely distinguishable features on the headset enables the user to verify the positioning of positioning indicator by feeling the positioning indicator simultaneously with feeling a centered part of her face, such as the nose bridge, without requiring visual assistance of a mirror or another person. However, positioning of the headset using the above positioning indicators may still be error-prone.

Accordingly, there is a need for alternative solutions on positioning of a headset for transcranial brain stimulation.

SUMMARY OF THE INVENTION

In view of the above, an objective of the invention is to solve or at least reduce one or several of the drawbacks discussed above. Generally, the above objective is achieved by the attached independent patent claims.

According to a first aspect a method of guiding positioning of electrodes for transcranial brain stimulation on a head of a user of the electrodes is provided. The method comprising: capturing, using a camera, one or more head images depicting the head; detecting, in the one or more head images, features of the head; creating, using the detected features of the head, a model of the head; computing, using the model of the head, intended positions of the electrodes on the head; and displaying, on a display, a representation of the electrodes as an overlay on an image of the head of the user.

A user of the electrodes for transcranial brain stimulation may film or photograph her head. By detecting features of the head of the user a model of the head may be created. The model may be a 2D or 3D model depending on what kind of images are available. After having created the model of the head of the user a correct position of the electrodes relative the head of the user may be overlaid on an image of the head of the user. This may guide the user to position the electrodes at correct positions relative the head of the user. Hence, a method for guiding the user of the electrodes to position the electrodes correctly is provided. This may allow for a higher quality transcranial brain stimulation. Further, this may allow for a user to correctly fit the electrodes, e.g. at home, without the need of a physician to be present. The electrodes may form part of a headset for transcranial brain stimulation. The headset may be any kind of support structure supporting the electrodes. According to one example, the headset may comprise a rigid frame. According to another example, the headset may be made of fabric, e.g. in the form of a headband or a cap. Hence, a method for guiding the user of a headset for transcranial brain stimulation to position the headset correctly is provided. An example of correct positioning of the electrodes is a positioning according to the 10-20 system or international 10-20 system. Alternative positioning of the electrodes is a positioning according to the 10-10 system or according to the Omni-Lateral-Electrode, OLE, system. By displaying, a representation of the electrodes as an overlay on an image of the head of the user, augmented reality may be used for positioning of the headset, especially the electrodes of.

The method may further comprise: capturing one or more electrode images depicting the head of the user of the electrodes wearing the electrodes; detecting, in the one or more electrode images, features of the electrodes; computing, using the model of the head and the features of the electrodes, a relative position of the head and the electrodes; in response to the relative position of the head and the electrodes being above a threshold, computing, using the model of the head and the features of the electrodes, a direction of adjustment of the electrodes relative the head; communicating, to the user, information pertaining to the direction of adjustment of the electrodes relative the head.

After a user has positioned the electrodes on the head she may film or photograph her head. By detecting features of the head of the user a model of the head may be created. The model may be a 2D or 3D model depending on what kind of images are available. By detecting features of the electrodes a current positioning of the electrodes relative the head of the user may be found. After having created the model of the head of the user and finding the current positioning of the electrodes relative the head of the user, a correct position of the electrodes relative the head of the user may be overlaid on an image of the head of the user and verification if the electrodes is correctly positioned may be found. This may guide the user to position the electrodes, and especially the electrodes thereof, at the correct position relative the head of the user. Hence, a method for guiding the user of the electrodes to position the electrodes correctly is provided. The positioning of the electrodes may further be verified to be a correct position. This may allow for a higher quality transcranial brain stimulation. Further, this may allow for a user to correctly fit the electrodes, e.g. at home, without the need of a physician to be present. It may further allow for hindering a start of a treatment session in case of the position of the electrodes is not verified as being correct. By displaying, a representation of the electrodes as an overlay on an image of the head of the user, augmented reality may be used for verifying that the positioning of the electrodes, especially the electrodes of, is made correctly.

The method may further comprise: in response to the relative position of the head and the electrodes being at or below the threshold, communicating, to the user, information pertaining to that the electrodes is correctly positioned.

The method may further comprise: comparing the created model of the head to a plurality of predetermined models of heads, wherein each predetermined model of a head comprises information pertaining to positioning of the electrodes for that particular predetermined model of the head; and finding one predetermined model of a head being a best fit between the created model of the head and the plurality of predetermined models of heads, wherein the act of compute the relative position of the head and the electrodes is further based on the one found predetermined model of a head.

The one or more electrode images may be a subset of the one or more head images. The one or more electrode images may be the same images as the one or more head images.

The method may further comprise: comparing the created model of the head to a plurality of predetermined models of heads, wherein each predetermined model of a head comprises information pertaining to positioning of the electrodes for that particular predetermined model of the head; and finding one predetermined model of a head being a best fit between the created model of the head and the plurality of predetermined models of heads, wherein the act of compute the intended electrodes position on the head is further based on the one found predetermined model of a head.

According to a second aspect a non-transitory computer-readable recording medium having recorded thereon a program comprising program code portions which when executed on an electronic device having processing capabilities is configured to perform the method according to the first aspect is provided.

The above mentioned features of the method when applicable, apply to this second aspect as well. In order to avoid undue repetition, reference is made to the above.

According to a second aspect a kit is provided. The kit comprises a headset for transcranial brain stimulation and a non-transitory computer-readable recording medium having recorded thereon a program which is executable on an electronic device having processing capabilities. The headset comprises a circuit comprising a first electrode and a second electrode. The program comprises program code portions which when executed on the electronic device is configured to: receive one or more head images depicting a head of a user of the headset; detect, in the one or more head images, features of the head; create, using the detected features of the head, a model of the head; compute, using the model of the head, an intended headset position on the head; and display, on a display, a representation of the headset as an overlay on an image of the head of the user.

The program may further comprise program code portions which when executed on the electronic device is configured to: receive one or more headset images depicting the head of the user of the headset wearing the headset; detect, in the one or more headset images, features of the headset; compute, using the model of the head and the features of the headset, a relative position of the head and the headset; in response to the relative position of the head and the headset being above a threshold, compute, using the model of the head and the features of the headset, a direction of adjustment of the headset relative the head; and communicate, to the user, information pertaining to the direction of adjustment of the headset relative the head.

The program may further comprise program code portions which when executed on the electronic device is configured to: in response to the relative position of the head and the headset being at or below the threshold, communicate, to the user, information pertaining to that the headset is correctly positioned. The communication, to the user, may be performed by displaying information on a display and/or announcing information via a loudspeaker.

The program may further comprise program code portions which when executed on the electronic device is configured to: compare the created model of the head to a plurality of predetermined models of heads wherein each predetermined model of a head comprises information pertaining to positioning of the headset for that particular predetermined model of the head, in order to find one predetermined model of a head being a best fit between the created model of the head and the plurality of predetermined models of heads; and wherein compute the intended headset position on the head and/or compute the relative position of the head and the headset, is further based on the one found predetermined model of a head.

The program may further comprise program code portions which when executed on the electronic device is configured to: capture, using a camera of the electronic device, the one or more headset images and/or the one or more head images.

The headset may further comprise: a wireless transceiver configured to wirelessly communicate with the electronic device; a power source configured to provide power to the circuit; and a controller being configured to control powering of the circuit according to the control signal.

The program may further comprise program code portions which when executed on the electronic device is configured to: store, in a computer memory, a schedule for performing transcranial brain stimulation, and generate a control signal for the headset such that transcranial brain stimulation is performed according to the schedule for performing the transcranial brain stimulation.

The above mentioned features of the method when applicable, apply to this third aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting.

It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE INVENTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
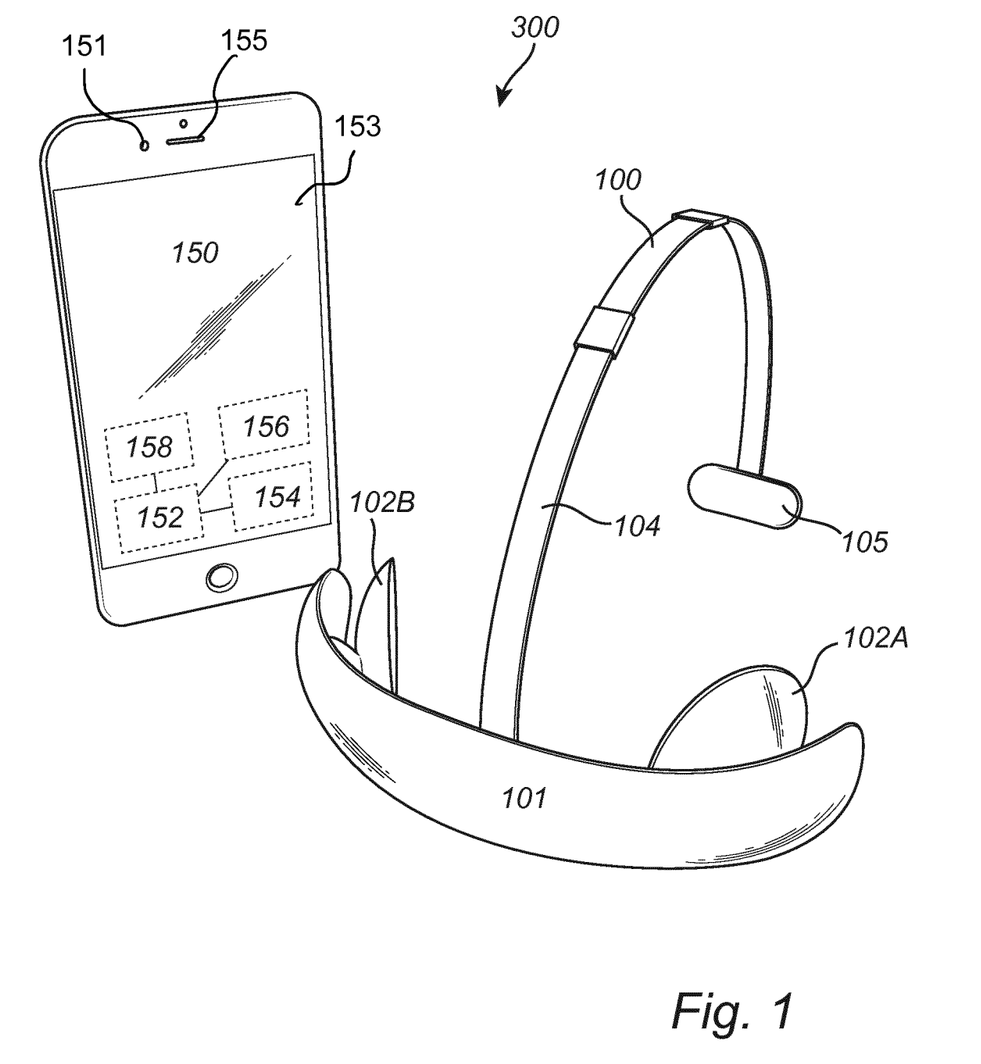
FIG. 1 illustrates a kit comprising a headset for transcranial brain stimulation and an electronic device configured to control the headset.

In FIG. 1, a kit 300 for transcranial brain stimulation is illustrated. The kit comprises a headset 100 for transcranial brain stimulation and a non-transitory computer-readable storage medium 154 having stored thereon a computer program being executable on a device having processing capabilities. The non-transitory computer-readable storage medium 154 is typically located in an electronic device 150. The non-transitory computer-readable storage medium 154 will in this context also be referred to as a memory of the electronic device 150. The memory 154 may be any type of non-transitory computer-readable storage medium which may persistently store digital information. The memory 154 may, e.g., be a solid state drive, a flash memory or any other device which may persistently store digital information. The electronic device 150 comprises a processor 152 and the non-transitory computer-readable storage medium 154. The electronic device may e.g. be a handheld electronic device, such as a laptop, a smartphone, a tablet, or a smartwatch. The processor 152 is configured to execute a computer program stored on the non-transitory computer-readable storage medium 154. Hence, the non-transitory computer-readable storage medium 154 having recorded thereon a computer program which is executable by the processor 152 of the electronic device 150. The electronic device 150 may further comprise a wireless transceiver 156. The wireless transceiver 156 is configured to establish a communication channel with the headset 100. The wireless transceiver 156 may be configured to wirelessly communicate with the headset 100. Any suitable wireless protocol, such as Bluetooth, Wi-Fi, ZigBee, or wireless USB, may be used. The electronic device 150 may further comprise a network communication unit 158. The network communication unit 158 is configured to establish a communication channel with a server via a computer network. The network communication unit 158 is preferably configured to communicate wirelessly with the server. Any suitable wireless protocol, such as 3G, 4G, 5G, or Wi-Fi, may be used. The communication between the electronic device 150 and the server and the communication between the electronic device 150 and the headset 100 is preferably independent of each other.

The computer program may be an application downloadable to the electronic device 150 via an application providing service. The computer program comprises code portions which when executed on the electronic device 150 is configured to perform different acts.

A code portion of the computer program may be configured to store a schedule for performing a transcranial brain stimulation in a computer memory. The schedule for performing transcranial brain stimulation may comprise information pertaining to how often and/or when the headset 100 is to be used for performing a session of the transcranial brain stimulation. This information may e.g. be indicative of a time window within a session of the transcranial brain stimulation is to be performed. The time window may e.g. be defined with a specific day or with some specific days. For example, this information may be indicative of that the session shall be performed between certain hours of a day, that the session shall be performed every second day, etc. The user may also be prompted to schedule the next session. Within the limits of the overall schedule. For instance, the user may be prompted to plan when he/she will do the next session. This may comprise information on time and/or day for the next session. This information may then be put into the schedule for performing a transcranial brain stimulation. Hence, the schedule may be updated. The user may then be reminded so that the next session is performed at the next scheduled session. In this way the user may influence the schedule.

The schedule for performing transcranial brain stimulation may further comprise information pertaining to how a specific session shall be composed. This information may e.g. be indicative of currents to be used for a specific stimulus within the specific session, intervals between stimuli of the specific session, duration of a stimulus of the specific session, duration of the specific session, etc.

The schedule for performing transcranial brain stimulation may moreover comprise information pertaining to displaying of video sequence to be watched in connection with receiving the transcranial brain stimulation, see below for more details. This information may e.g. be indicative of which video sequence to be displayed and how often.

The schedule for performing transcranial brain stimulation may furthermore comprise information pertaining to execution of cognitive games to be played in connection with receiving the transcranial brain stimulation. This information may e.g. be indicative of which games to be executed and how often.

The schedule for performing transcranial brain stimulation may further comprise information pertaining to prompting the user to input information pertaining to status of the user. This information may e.g. be indicative of how often information pertaining to status of the user shall be prompted for. This provide the possibility for remote review of the status of the user. For example, the health of the user may be monitored in a continent manner without the need for a physician at the site of the user.

The computer memory onto which the schedule for performing the transcranial brain stimulation is stored may be a memory of the electronic device 150, for example, the non-transitory computer-readable storage medium 154. Alternatively, the computer memory may be a memory of the headset 100. Yet alternatively, the computer memory may be a memory of a server. Yet alternatively, the schedule for performing the transcranial brain stimulation may be stored at a plurality of the above mentioned computer memories. Further, alternatively, the schedule for performing the transcranial brain stimulation may be stored distributed on a plurality of the above mentioned computer memories. Hence, different portions of the schedule may be stored on different memories, the storing of the schedule may be distributed over a plurality of memories. For example, the information pertaining to how often and/or when the headset is to be used for performing a session of the transcranial brain stimulation may be stored on the memory of the electronic device and the information pertaining to how a specific session shall be composed may be stored on the memory of the headset. The full schedule for performing the transcranial brain stimulation may be stored on the server.

A code portion of the computer program may be configured to generate a control signal for the headset 100. The control signal comprising information pertain to how to control the headset 100 such that transcranial brain stimulation is performed according to the schedule for performing the transcranial brain stimulation. The control signal may be seen as a, from the schedule, generated control signal, wherein the control signal is generated at the electronic device 150. This, at the electronic device 150 generated, control signal may then be sent from the electronic device 150 to the headset 100. A controller 210 of the headset may then be configured to control a transcranial brain stimulation according to the received control signal. Alternatively, or in combination, the control signal may be seen as an extraction of a portion of the schedule for performing the transcranial brain stimulation, wherein the portion comprises information pertain to how to control the headset 100 such that transcranial brain stimulation is performed. The portion of the schedule may then be sent from the electronic device 150 to the headset 100. The controller 210 of the headset may then be configured to control a transcranial brain stimulation according to the received portion of the schedule.

A code portion of the computer program may be configured to prompt a user of the electronic device to identify herself. By this it may be safeguarded that the headset for transcranial brain stimulation may only be used by users intended to use it.

A code portion of the computer program may further be configured to remind the user to use the headset according to the schedule for performing the transcranial brain stimulation. Reminding the user when the user shall use the headset 100 counteracts negligence or unwitting non-compliance, e.g. due to misunderstanding or miscommunication, in relation to the therapy on account of the patient. The reminder may be prompted to the user using one or more of a loudspeaker 155 of the electronic device 150, a light source of the electronic device 150, a vibrator of the electronic device 150 and a display 153 of the electronic device 150. For example, the user may be prompted by a message displayed on the display of the electronic device 150. Alternatively, or in combination, the reminder may be prompted to the user using one or more of a loudspeaker 216, a light source 218 and a vibrator 220 of the headset 100. The loudspeaker 216, the light source 218 and the vibrator 220 of the headset 100 will be discussed in more detail below. This provides a kit for performing transcranial brain stimulation where the user can be conveniently prompted to wear the headset and signaled when to remove it. This provides a safety measure against over-use of the headset by the user due to negligence or ignorance. Further, by scheduling the use of the headset for transcranial brain stimulation the usage may be limited according to the schedule. In this way over-use may be avoided. If the user tries to over-use the headset the kit may indicate this by issuing an error-message. The error message may be issued via a display 155 of the electronic device 150. The schedule for performing the transcranial brain stimulation may comprise information pertaining to the frequency of usage of the headset for performing the transcranial brain stimulation. For example, one session per day, one session per every second day, X sessions per every week, etc.

A code portion of the computer program may further be configured to display information on the display 155 of the electronic device 150 in accordance with a schedule for displaying information. The schedule for displaying information may relate to the schedule for performing the transcranial brain stimulation. The displayed information may e.g. be a video sequence to be watched in connection with receiving the transcranial brain stimulation. The video sequence may be video lesson being part of a treatment program. The video sequence may be an instructions video instructing the user how to put on and use the headset 100.

A code portion of the computer program may further be configured to execute cognitive games. The user of the kit 300 may for example be prompted to play a cognitive game during the transcranial brain stimulation. When to participate in the cognitive game and/or when to be exposed to a video lesson may be part of the schedule for displaying information. This allow for setting up of a therapy program comprising both the actual transcranial brain stimulation but also to include viewing of videos and/or participation in cognitive games during or in between specific transcranial brain stimulation sessions. Hence, a kit providing enhanced treatment programs is provided.

A code portion of the computer program may further be configured to prompt the user to input information pertaining to status of the user. The user may be prompted by displaying a message on the display of the electronic device 150. The input information prompted for may be information pertaining to information about the user's current health. For example, information according to Phq-9, Hamilton Rating Scale for Depression (HRSD), Beck Depression Inventory (BDI, BDI-1A, BDI-II), Montgomery Åsberg Depression Rating Scale (MADRS, MADRS-s), Young Mania Rating Scale (YMRS) or any other psychiatric rating scale may be prompted for. The input information prompted for may further be one or more of information pertaining to age of the user, sex of the user, intake of pharmaceuticals of the user, training habits of the user, eating habits of the user, sleeping habits of the user, the geographical location of the user, the user's relationship to their surrounding family/friends and working situation of the user.

The user may input such information through input means of the electronic device. An example of an input means is a keyboard (virtual on a touch screen or realized as mechanical buttons). The input information pertaining to status of the user may then be stored in the computer memory. The computer memory used for storing the input information pertaining to status of the user may be the memory of the server. The input information pertaining to status of the user may then be provided to a physician for reviewing the schedule for the transcranial brain stimulation of the user.

A code portion of the computer program may further be configured to store information pertaining to performed transcranial brain stimulation in a computer memory. The computer memory may be the computer memory of the server. The information pertaining to performed transcranial brain stimulation may then be provided to a physician for reviewing the schedule for the transcranial brain stimulation of the user of the kit 300. Hence, means for monitoring the patient's progress through the therapy is provided. This further reduces the need for involvement of a physician upon performing the transcranial brain stimulation.

By being provided with the input information pertaining to status of the user and the information pertaining to performed transcranial brain stimulation the physician is provided with the possibility to assess the progress of the user and to make any adjustments required to the user's schedule for transcranial brain stimulation as well as inform the user that such adjustments have been made.

A code portion of the computer program may further be configured to update the schedule for performing the transcranial brain stimulation. This gives the possibility, for e.g. the physician, to adjust the schedule for transcranial brain stimulation. This provide the possibility for remote update of the schedule for performing the transcranial brain stimulation. This further reduces the need for involvement of a physician at the site of the user upon performing the transcranial brain stimulation.

Code portions of the computer program may further be configured to guide a positioning of the headset 100 on a head of a user of the headset 100. In the below description correct positioning of the headset 100 comprising electrodes will be discussed. It is however to be understood that it is the positioning of the electrodes that is of most importance. However, if the headset is correctly positioned also the electrodes are correctly positioned. An example of correct positioning of the electrodes is a positioning according to the 10-20 system or international 10-20 system. Alternative positioning of the electrodes is a positioning according to the 10-10 system or according to the Omni-Lateral-Electrode, OLE, system.

The guiding of the positioning of the headset 100 is based on that the user is capturing one or more images of her head. That is, the code portions are prompting the user to capture one or more images of the user's head. The one or more images are normally captured with the headset 100 being donned. Hence, the user may be prompted to film or photograph her head. Especially, the user may be prompted to film or photograph her head after the headset has been donned. A camera 151 of the electronic device 150 may be used for capturing the one or more images. From the one or more images being filmed or photographed, at least some of them are received, by the code portions of the computer program being configured to guide the positioning of the headset 100, as one or more head images. The one or more head images are depicting the head of the user of the headset 100. In the one or more head images, features of the head are detected. Using the detected features of the head a model of the head may be created.

The model of the head may be made using various methods. Below two examples of such methods will be discussed. First an example based on a 2D scheme and thereafter an example based on a 3D scheme.

Using the 2D scheme, a face within the one or more head images may be detected using a face detection algorithm (e.g., using Haar cascades classifier or neural network). Features of the head may thereafter be found using face key points detection (eyes, mouth, nose, face outline using Active shape model, neural network). Using the face key points, a model of the head may be created. For example, a parametric face model may be mapped to the detected key points.

The 3D scheme operates on a sequences of images. For example, the user may be prompted to sweep the camera in front of the head. The camera can be single image camera or a stereo camera. Based on the sequences of images a Visual Inertial Odometry to track the motion of the camera in space (egomotion) may be performed. Features of the head may be detected, using e.g., Haar cascades classifier or neural network. A model of the head may be created based on the image sequence using the known egomotion of the camera and features of the head.

Both for the 2D and 3D schemes, using the model of the head, an intended headset position on the head may be computed. Thereafter a representation of the headset may be presented as an overlay on an image of the head of the user.

Both for the 2D and 3D schemes, a plurality of predetermined models of heads may exist. Each predetermined model of a head may comprise information pertaining to positioning of the headset for that particular predetermined model of the head. Hence, the predetermined models of heads contain information of how the headset 100, and especially the electrodes of the headset, shall be positioned for various head sizes/shapes. The intended headset position on the head may be computed by finding a best fit between the plurality of predetermined models of heads and the created model of the head.

Hence, a representation of the headset being correctly positioned may then be overlaid on a camera image to guide the user to position the headset, and especially the electrodes thereof, at the correct position. Alternatively, or in combination, a representation of the headset being correctly positioned may then be overlaid as a virtually projection on top of the head of the user in an image of augmented reality glasses being worn by the user of the headset.

The code portions configured to guide the positioning of the headset 100 on the head of the user of the headset 100 may further be configured to detect the headset 100 position, especially the electrodes thereof, in the one or more captured images and verify the position of the headset 100 towards the model of the head. Hence, from the one or more images being filmed or photographed, at least some of them are received, by the code portions of the computer program being configured to guide the positioning of the headset 100, as one or more headset images. The one or more headset images are depicting the head of the user of the headset 100 wearing the headset 100. In the one or more headset images, features of the headset are detected. Using the detected features of the headset a model of the headset 100 may be created. Hence, both the model of the head and the model of the headset may be mapped to the same image and their relative position in 2D or 3D may be compared.

Using the model of the head and the features of the headset 100 a relative position of the head and the headset may be computed. Hence, the position of the headset 100 donned on the head of the user may be determined. Especially the position of the electrodes 102A, 102B of the headset 100 being donned on the head on the user may be determined. From this the correctness of the positioning of the headset 100, especially the electrodes 102A, 102B thereof, on the head of the user may be determined. A verification of correct positioned headset may be made. In case the headset is not correctly positioned the user may be prompted to adjust the positioning of the headset 100, especially the electrodes thereof. For example, in response to the relative position of the head and the headset being above a threshold, a direction of adjustment of the headset relative the head may be computed. The direction of adjustment may be computed using the model of the head and the features or model of the headset 100. The direction of adjustment of the headset relative the head may be in relative or direct terms. Hence, the user may be prompted to move the headset in a certain direction relative the head either by communicating in relative terms, e.g. move up the headset 100 upwards, downwards, to the left, to the right, etc., or by communicating in direct terms e.g. move up the headset 100 xcm upwards, ycm downwards, zcm to the left, kcm to the right, etc.

Accordingly, information pertaining to the direction of adjustment of the headset relative the head may then be communicated, to the user. The communication, to the user, may be performed by displaying information on a display. The display may be the display 153 of the electronic device 150 or a display of augmented reality glasses. Alternatively, or in combination, the communication, to the user, may be performed by announcing information via a loudspeaker. The loudspeaker may be the loudspeaker 216 of the headset 100 and/or a loudspeaker 155 of the electronic device 150. Further, in response to the relative position of the head and the headset being at or below the threshold, information pertaining to that the headset 100 is correctly positioned may be communicate to the user. This information may also be regarded as information pertaining to the direction of adjustment of the headset relative the head may then be communicated. In this case, the direction of adjacent corresponds to no adjustment. Also the information pertaining to that the headset 100 is correctly positioned may be communicate to the user by displaying information on a display and/or announcing information via a loudspeaker, just as discussed above for the adjustment information.

By this the user of the headset may be visually and/or by audio guided towards a correct position of the headset 100. Further, a correct positioning of the headset 100 may be validated before a transcranial brain stimulation session is allowed to start. This kind of verification of correct positioning of the headset 100 on the head of the user may be used as a mandatory step before each transcranial brain stimulation session to make sure that the user has positioned the headset 100, especially the electrodes thereof, in the correct position.

Figure 3:
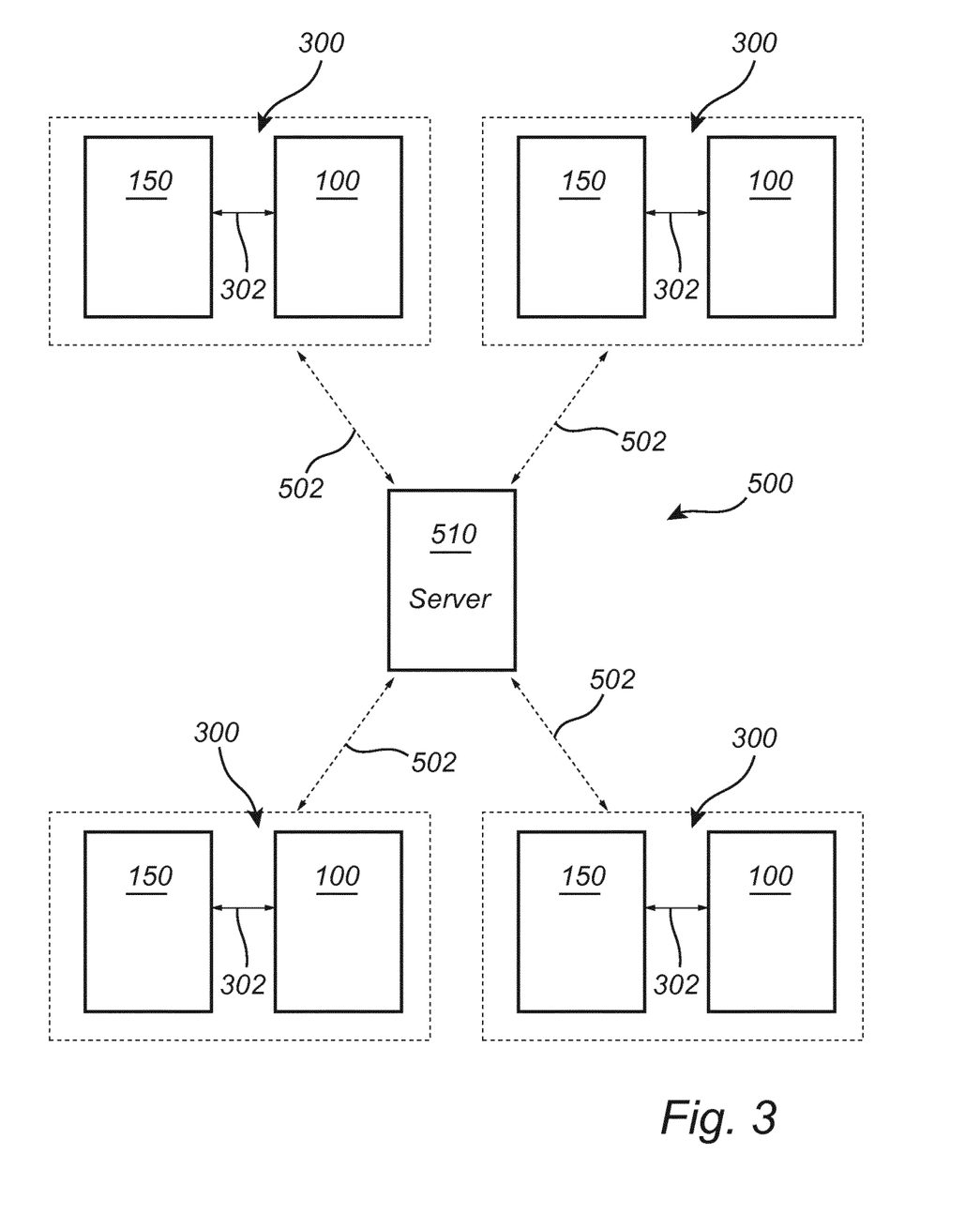
FIG. 3 illustrates a system for transcranial brain stimulation comprising a plurality of kits and a server.

Further, head images and or headset images and data about head sizes and placement of the headset may be collected and sent to a server 510, see FIG. 3. This allows a physician to monitor a user's usage of the headset.

FIG. 3 illustrates a system 500 comprising a server 510 and a plurality of kits 300. The server 510 is configured to individually communicate with the each of the plurality of kits 300. The communication is realized by establishing communication channels 502 over a computer network or cellular network. As mentioned above the communication channels 502 between the server 510 and an electronic device 150 of a kit 300 is independent from a communication channel 302 between the electronic device 150 of a kit 300 and a headset 100 of the kit 300. The server 510 is configured to communicate with the electronic devices 150 in each of the plurality of kits 300. Such a system 500 facilitates centralized planning of schedules for transcranial brain stimulation. Such a system 500 also facilitates centralized evaluation of the performed treatment program comprising the transcranial brain stimulation and possibly also watching of video lessons, playing of cognitive games, etc. Hence, the system 500 facilitates usage of the kit 300 for transcranial brain stimulation in a home environment with reduced need of in person consultation with a physician.

Further, the input information pertaining to status of the user may be correlated with the information pertaining to performed transcranial brain stimulation. Such correlated information may be stored at the server 510. The correlation may be made by program code portions at the different electronic devices 150 or at the server 510. Further, such correlated information may be used for training e.g. an artificial neural network to determine a schedule for performing transcranial brain stimulation based on information pertaining to status of a user a kit 300 for transcranial brain stimulation. For the transcranial brain stimulation to be as effective as possible the transcranial brain stimulation (and possibly also thereto associated cognitive games and/or video lessons, scheduling and motivational functions being part of a treatment program) is to be adapted to the individual user. Different users respond differently to the amount and order of brain stimulation, video lessons and/or cognitive games. Therefore, the transcranial brain stimulation, the video lessons and/or cognitive games is to be optimally controlled per user. A decision engine may be used for performing this control. The decision engine may comprise both hardcoded rules and learned rules. An example of such a decision engine is an engine based on reinforcement learning. The decision engine may use individual traits and/or treatment history as input for determining a schedule for transcranial brain stimulation. As mentioned above the input/output mapping of the decision engine may partly be based on hardcoded rules and partly on learned rules. The hardcoded rules may be derived from domain knowledge, for example in what order videos should be presented and how often the user shall be prompted to input information pertaining to status of the user. The learned rules may be derived using machine learning, for example based on reinforcement learning, supervised learning or unsupervised learning. The learning part may, as mentioned above, be based on an artificial intelligence paradigm called reinforcement learning with the goal to detect nonobvious decision rules from large quantities of user data. Reinforcement learning deals with problems where the outcome of a sequence of actions is delayed, which is what we have in our case. The actions of the decision engine are recommendations to the user, and the outcome we want to optimize for may be a subjective self-rating score of the user at the end of a treatment program comprising the transcranial brain stimulation. Important to note here is that we can't measure how good each recommendation is in itself, but instead only get to know the end outcome of a long sequence of recommendations. Reinforcement learning is a collection of methods to optimize these kind of decision sequences, by penalizing bad decisions and promoting good decisions based on an end outcome.

Figure 2:
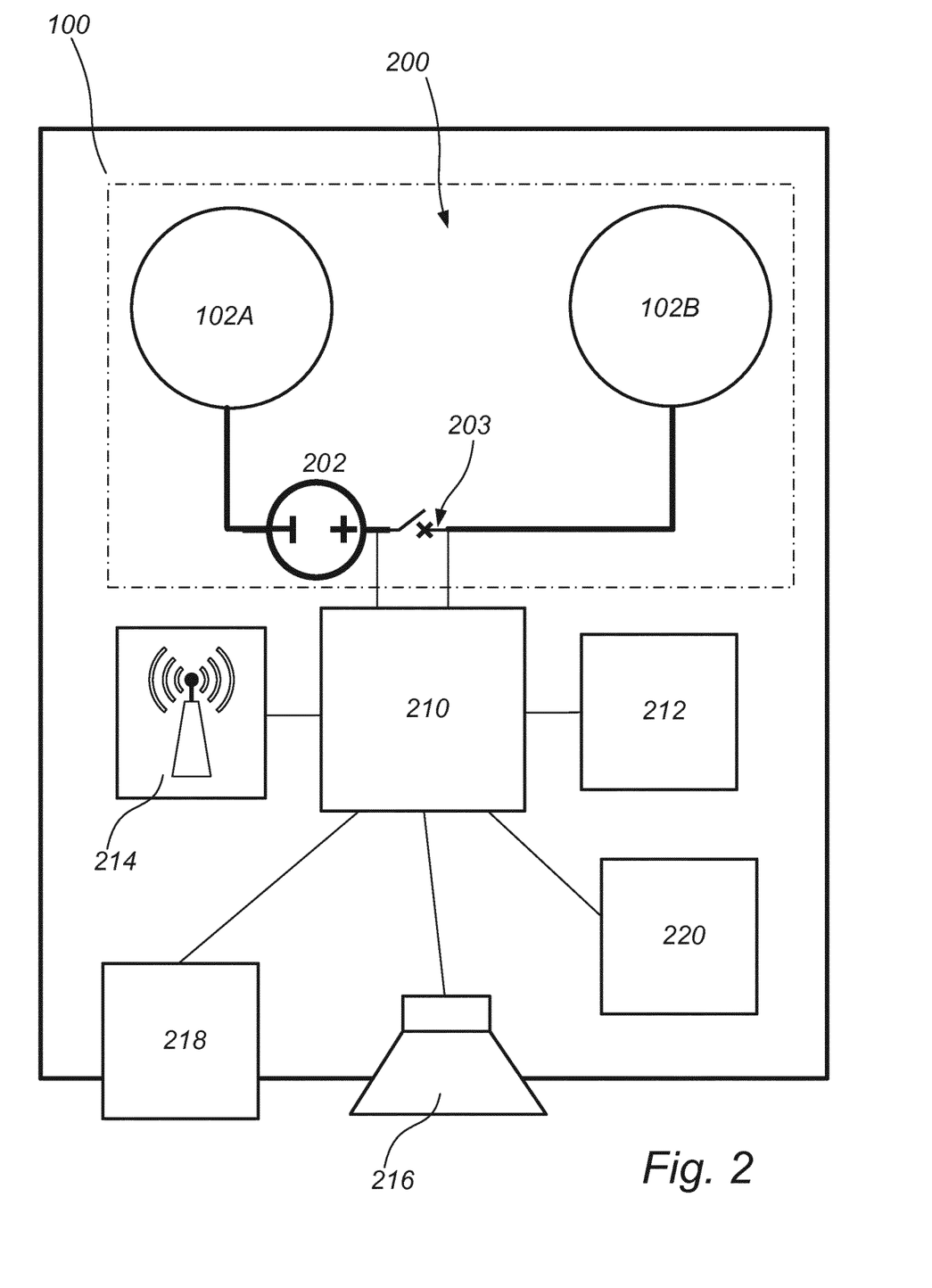
FIG. 2 is a schematic sketch of a headset for transcranial brain stimulation.

In connection with FIG. 2 the headset will be discussed in more detail. The headset comprises first and second electrodes 102A, 102B. The first and second electrodes 102A, 102B are comprised in a circuit 200. The circuit 200 is configured to be powered according to a schedule for performing transcranial brain stimulation. The first and second electrodes 102A, 102B are connected in the circuit 200. The circuit 200 further comprises a power source 202 and a switch 203. Upon the headset 100 being worn by the user and upon the switch 203 is engaged, a closed circuit comprising the first and second electrodes 102A, 102B, the user's forehead and the power source 202 is formed. This allows current to flow through the user's cranium. The power source 202 may be a battery. The battery may be a chargeable battery.

The headset 100 may further comprise a controller 210. The controller 210 is configured to periodically power the circuit 200 according to a schedule for performing transcranial brain stimulation. Thereby a current is periodically provided to user's brain for performing the transcranial brain stimulation. The controller 210 is configured to periodically control the switch 203. The controller 210 may be hardware or software implemented. The controller 210 may comprise a microcontroller, a system of microcontrollers, or any type of processor or control circuit which can engage and disengage the switch 202. This provides a headset 100 which may vary the electric impulses to the head of the user according to schemes for transcranial brain stimulation.

The headset 100 may further comprise a memory 212. The memory may be any type of non-volatile memory configured to store digital data. The memory 212 may, e.g., be a solid state drive, a flash memory or any other device which can persistently store digital information. The memory 212 may, e.g., be configured to store a schedule for performing the transcranial brain stimulation, or at least a portion of the schedule for performing the transcranial brain stimulation. Especially, the portion of the schedule for performing the transcranial brain stimulation comprising information pertaining to how a specific session shall be composed, this information may e.g. be indicative of currents to be used for a specific stimulus within the specific session, intervals between stimuli of the specific session, duration of a stimulus of the specific session, duration of the specific session, etc. Hence, the schedule for performing the transcranial brain stimulation may comprise information pertaining to when to open and close the switch 203. Further, the portion of the schedule for performing the transcranial brain stimulation stored on the memory 212 of the headset 100 may comprise information pertaining to when the user shall wear the headset 100 in order to receive the transcranial brain stimulation. The controller 210 may be arranged to read data from the memory 212. Hence, the controller 210 may be configured to receive information from the memory 212 on the schedule for performing the transcranial brain stimulation. However, it is realized that the schedule for transcranial brain stimulation, or at least portions of the schedule for transcranial brain stimulation, may be stored elsewhere in some other memory accessible by the controller 210. For example, the controller 210 may be arranged to receive data from other memories. The controller 210 may be arranged to receive data from the electronic device 150. The controller 210 may be arranged to receive data from the server 510. The controller 210 may further be configured to write data to the memory 212. Hence, the controller 210 may be configured to write data to the memory 212 pertaining to performed transcranial brain stimulation. Hence, means for monitoring the patient's progress through the therapy is provided. This further reduces the need for involvement of a physician upon performing the transcranial brain stimulation. The controller 210 may be configured to write data to the memory 154 of the electronic device 150. This may be made by sending the information to be stored at the electronic device 150, via a wireless transceiver 214 of the headset 100, to the electronic device 150. The wireless transceiver 214 is configured to wirelessly communicate with the electronic device 150. Any suitable wireless protocol, such as Bluetooth, Wi-Fi, ZigBee, or wireless USB, may be used. Hence, a wireless communication channel may be established between the wireless transceiver 214 of the headset 100 and the wireless transceiver 156 of the electronic device 150.

The wireless communication channel between the wireless transceiver 214 of the headset 100 and the wireless transceiver 156 of the electronic device 150 may further be used by the controller 210 of the headset 100 to receive data from the electronic device 150. For example, data stored on the memory 154 of the electronic device 150, e.g. data relating to the schedule for transcranial brain stimulation. Further, the wireless communication channel between the wireless transceiver 214 of the headset 100 and the wireless transceiver 156 of the electronic device 150 may be used by the controller 210 of the headset 100 to receive data routed by the electronic device 150. For example, data stored on the memory of the server 510 that are sent to the controller 210 via the electronic device 150. An example of data that may be routed by the electronic device 150 is data relating to the schedule for transcranial brain stimulation that are stored on the memory of the server 510. Moreover, the controller 210 may be configured to write data to the memory of the server 510. Even that kind of data may be routed via the electronic device 150. The data written to the memory of the server 510 may be data pertaining to performed transcranial brain stimulation.

As was briefly mentioned above, the headset 100 may further be configured to signal when the user shall wear or take off the headset 100 for receiving the transcranial brain stimulation. Signaling to the user when the user shall wear or take off the headset 100 counteracts negligence or unwitting non-compliance, e.g. due to misunderstanding or miscommunication, in relation to the therapy on account of the patient. The signaling can be done in many different ways. For this purpose, the headset 100 may comprise a speaker 216. The controller 210 may be configured to control the speaker 216. The speaker 216 is configured to emit sound pertaining to information reminding the user to wear or remove the headset 100. Some non-limiting examples of sounds are beeping sounds and voice synthesis. The loudspeaker 216 may be arranged in the forehead frame 101. The headset 100 may comprise a light source 218. The light source 218 may e.g. comprise one or more LED:s. The controller 210 may be configured to control the light source 218. The light source 218 is configured to emit light pertaining to information reminding the user to wear or remove the headset 100. For example, the light source 218 may be configured to emit light having different colors for reminding the user to wear or remove the headset 100. The light source 218 may be configured to emit light pulses of different frequency to remind the user. The light source 218 may be arranged in the forehead frame 101. The headset may comprise a vibrator 220. The controller 210 may be configured to control the vibrator 220. The vibrator 220 is configured to emit vibrate in order to remind the user to wear or remove the headset 100. The vibrator may be arranged in the forehead frame 101. Any combination of the loudspeaker 216, the light source 218 or the vibrator 220 may be used for reminding the user to wear or remove the headset 100. Hence, just one of them, two of them, or all of them may be used for reminding the user to wear or remove the headset 100.

The headset 100 may be designed any various ways. One example of a headset design is illustrated in FIG. 1. According to this exemplified design, the headset 100 comprises a forehead frame 101 and a bracket 104. The shape of the forehead frame 101 is designed to fit a forehead of a user of the headset 100. The forehead frame is designed as a single member. This member is shaped as an elongated arch. Hence, the forehead frame 101 is defining an elongated arch. This allows the forehead frame 101 to follow approximately the shape of the forehead of the user when placed on the head. The forehead frame 101 may be manufactured by e.g. plastic, composite materials, metal or any other suitable material.

The forehead frame 101 is configured to support the first and second electrodes 102A, 102B. The forehead frame 101 is configured to support the bracket 104. The first electrode 102A is arranged at a first end portion of the forehead frame 101. The second electrode 102B is arranged at a second end portion of the forehead frame 101. Hence, the first and second electrodes 102A, 102B are placed on the forehead frame 101 such that when the forehead frame 101 is worn by the user, the first and second electrodes 102A, 102B will come in contact with the forehead on either side of the user's head.

The bracket 114 is arranged at a center portion of the forehead frame 101. The bracket 104 may be arranged to the forehead frame 101 in any suitable way. For example, the bracket 104 may be screwed, glued or fastened in any other suitable way to the fore head frame 101. In this context the phrase "center portion" should be understood to refer to any part of the longitudinal extension of the forehead frame 101 which lies between the first and second electrodes 102A, 102B. The bracket 104 has a longitudinal extension which, when the headset 100 is used, extends from the forehead of the user towards the back of the user's head. In this way, the bracket 104 ensures that the user wears the headset 100 such that the first and second electrodes 102A, 102B come in contact only with their respective side of the user's forehead. The bracket 104 may be constructed such that its extension from the frame is variable, ensuring a better fit for the user. This can be achieved in many ways, which the skilled person understands. Alternatively, the bracket 104 may be of fixed length. The bracket 104 may further comprise a support cushion 105 arranged at an end portion of the bracket 104 being opposite to where the bracket 104 is arranged at the forehead frame 101. The cushion 105 makes the bracket 104 more comfortable for the user.

The in FIG. 1 illustrated exemplified headset 100 provides a headset for performing transcranial brain stimulation wherein the electrodes are unlikely to be placed incorrectly on the forehead of the user. This has the advantage of allowing for transcranial brain stimulation to be performed without a physician available to place the electrodes on the head of the patient. Furthermore, the headset may be designed to be lightweight and comfortable, eliminating the need for fabric headwear which may be warm and uncomfortable when worn for extended periods of time. This further provides a comfortable headset which is impossible to mount such that the direction of the current is reversed, which may be critical in for example transcranial direct current stimulation, tDCS. During electrical transcranial brain stimulation, the potential of neuronal cells is influenced by an applied electric field. This field influences the neuronal cells under the stimulated area and pushes them closer or further away from their activation threshold.

The first and second electrodes 102A, 102B may be configured to pivot to some degree. Thus, a headset 100 is provided where the major surface of each electrode 102A, 102B is pivoted to be principally parallel to the surface of the forehead of the user. The first and second electrodes 102A, 102B need not be configured to pivot. A more comfortable headset which is adaptable to many different shapes of patient foreheads and reduces the need for size adaptability of the headset is provided.

The first and second electrodes 102A, 102B may be of any type of conducting material suitable for repeated use. Alternatively, the first and second electrodes 102A, 102B may be configured for one-time use only, in which case they are to be replaced by the user between uses.

The first and second electrodes 102A, 102B may comprise an adhesive layer. The adhesive layer may be discarded after use. The adhesive layer ensures proper contact between the electrode and the forehead of the user while also providing a hygienic solution. For example, the adhesive layer may ensure that the headset 100 does not drift during use, securing it in place on the head of the patient.

The headset 100 may of course be provided with further electrodes, in case the desired scheme for transcranial brain stimulation so requires.

For some schemes of transcranial brain stimulation, the first and second electrodes 102A, 102B correspond to a first and second side of the user's forehead, respectively. By this is meant that each electrode 102A, 102B is configured to be brought into contact only with either the left or the right side of the user's forehead.

The kit provides the possibility for a user to perform a transcranial brain stimulation therapeutic schedule themselves with the aid of an electronic device, limiting the need for visits to or by a physician. The headset does not need to be wired to any controller, improving portability of the headset and increasing user comfort and convenience.

The in FIG. 1 illustrated example of a headset 100 is just one example of a headset 100 that may be used in the kit 300 or system 500 for transcranial brain stimulation disclosed herein. The headset 100 may be designed in many different alternative ways. According to one example, the headset 100 may not comprise the bracket 114 but only the forehead frame 101. According to another example, the headset 100 is a conventional fabric headwear.

Figure 4:
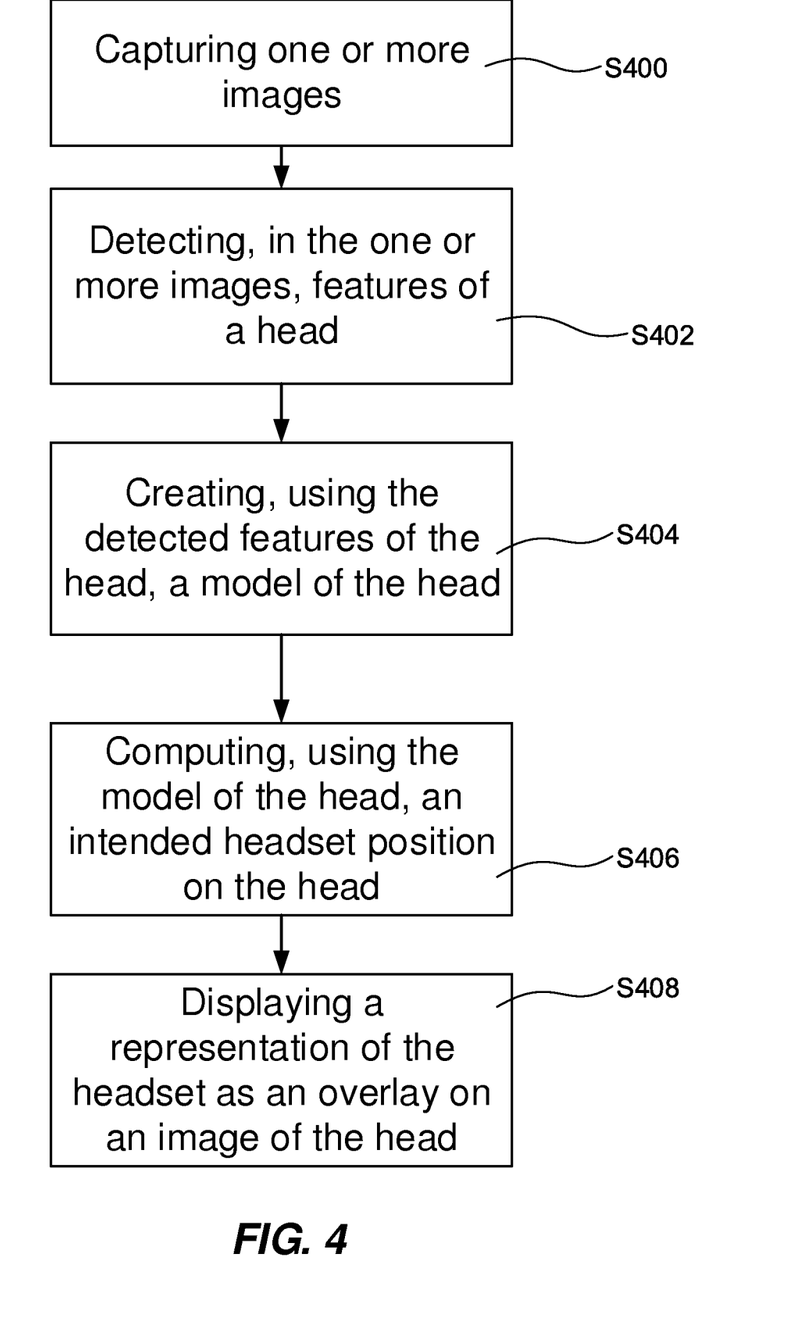
FIG. 4 is a block diagram of a method of guiding positioning of the headset for transcranial brain stimulation on a head of a user of the headset.

With reference to FIG. 4 a method of guiding positioning of the headset 100 for transcranial brain stimulation on a head of a user of the headset 100 will be discussed. The method comprises one or more of the following acts. The acts may be performed in any order suitable.

Capturing S400 one or more head images depicting the head of the user of the headset 100. The capturing S400 may be made by a digital camera configured to capture still image. The capturing S400 may be made by a digital camera configured to capture video images. The camera may be a single image camera or a stereo camera. The one or more images is depicting the head of the user. The one or more head images may be a plurality of head images. At least some of the plurality of head images may be headset images depicting the head of the user of the headset 100 wearing the headset 100. Hence, one or more headset images may be captured.

Detecting S402, in the one or more head images, features of the head. The features of the head may be eyes, mouth, nose, and/or face outline. The features may be detected using an active shape model or a neural network.

Creating S404, using the detected features of the head, a model of the head.

Computing S406, using the model of the head, an intended headset position on the head. The act of computing S406 may comprise comparing the created model of the head to a plurality of predetermined models of heads, wherein each predetermined model of a head comprises information pertaining to positioning of the headset for that particular predetermined model of the head; and finding one predetermined model of a head being a best fit between the created model of the head and the plurality of predetermined models of heads.

Displaying S408, on a display, a representation of the headset as an overlay on an image of the head of the user. The image of the head of the user may be an image of the one or more head images or an image of the one of more headset images. The display may be the display 153 of the electronic device 150 or a display of augmented reality glasses.

A user of the headset may use the electronic device 150 to film or photograph her head. By detecting features of the head of the user a model of the head may be created. The model may be a 2D or 3D model depending on what kind of images are available from the electronic device 150. After having created the model of the head of the user a correct position of the headset relative the head of the user may be overlayed on an image of the head of the user. This will guide the user to position the headset, and especially the electrodes thereof, at a correct position relative the head of the user.

The method of guiding positioning of the headset 100 for transcranial brain stimulation on a head of a user of the headset 100 may further comprise one or more of the following acts. The acts may be performed in any order suitable.

The act of capturing S400 may comprise capturing one or more headset images depicting the head of the user of the headset 100 wearing the headset 100.

Detecting, in the one or more headset images, features of the headset 100. The features of the headset may e.g. comprise the electrodes 102A, 102B thereof.

Computing, using the model of the head and the features of the headset 100, a relative position of the head and the headset 100. The act of computing a relative position of the head and the headset 100 may comprise comparing the created model of the head to a plurality of predetermined models of heads, wherein each predetermined model of a head comprises information pertaining to positioning of the headset 100 for that particular predetermined model of the head, and finding one predetermined model of a head being a best fit between the created model of the head and the plurality of predetermined models of heads.

In response to the relative position of the head and the headset 100 being above a threshold, computing, using the model of the head and the features of the headset, a direction of adjustment of the headset relative the head. The direction of adjustment of the headset relative the head may be in relative or direct terms. Hence, the user may be prompted to move the headset in a certain direction relative the head either by communicating in relative terms, e.g. move up the headset 100 upwards, downwards, to the left, to the right, etc., or by communicating in direct terms e.g. move up the headset 100 xcm upwards, ycm downwards, zcm to the left, kcm to the right, etc.

Communicating, to the user, information pertaining to the direction of adjustment of the headset 100 relative the head. The act of communicating, to the user, may be performed by displaying information on a display and/or announcing information via a loudspeaker. The display may be the display 153 of the electronic device 150 or a display of augmented reality glasses. The loudspeaker may be the loudspeaker 216 of the headset 100 or a loudspeaker 155 of the electronic device 150.

The act of communicating may further comprise, in response to the relative position of the head and the headset 100 being at or below the threshold, communicating, to the user, information pertaining to that the headset is correctly positioned.

After a user has positioned the headset 100 on the head she may use the electronic device 150 to film or photograph her head. By detecting features of the head of the user a model of the head may be created. The model may be a 2D or 3D model depending on what kind of images are available from the electronic device 150. By detecting features of the headset a current positioning of the headset relative the head of the user may be found. After having created the model of the head of the user and finding the current positioning of the headset relative the head of the user, a correct position of the headset relative the head of the user may be overlayed on an image of the head of the user and verification if the headset is correctly positioned may be found. This will guide the user to position the headset, and especially the electrodes thereof, at the correct position relative the head of the user.

Figure 5:
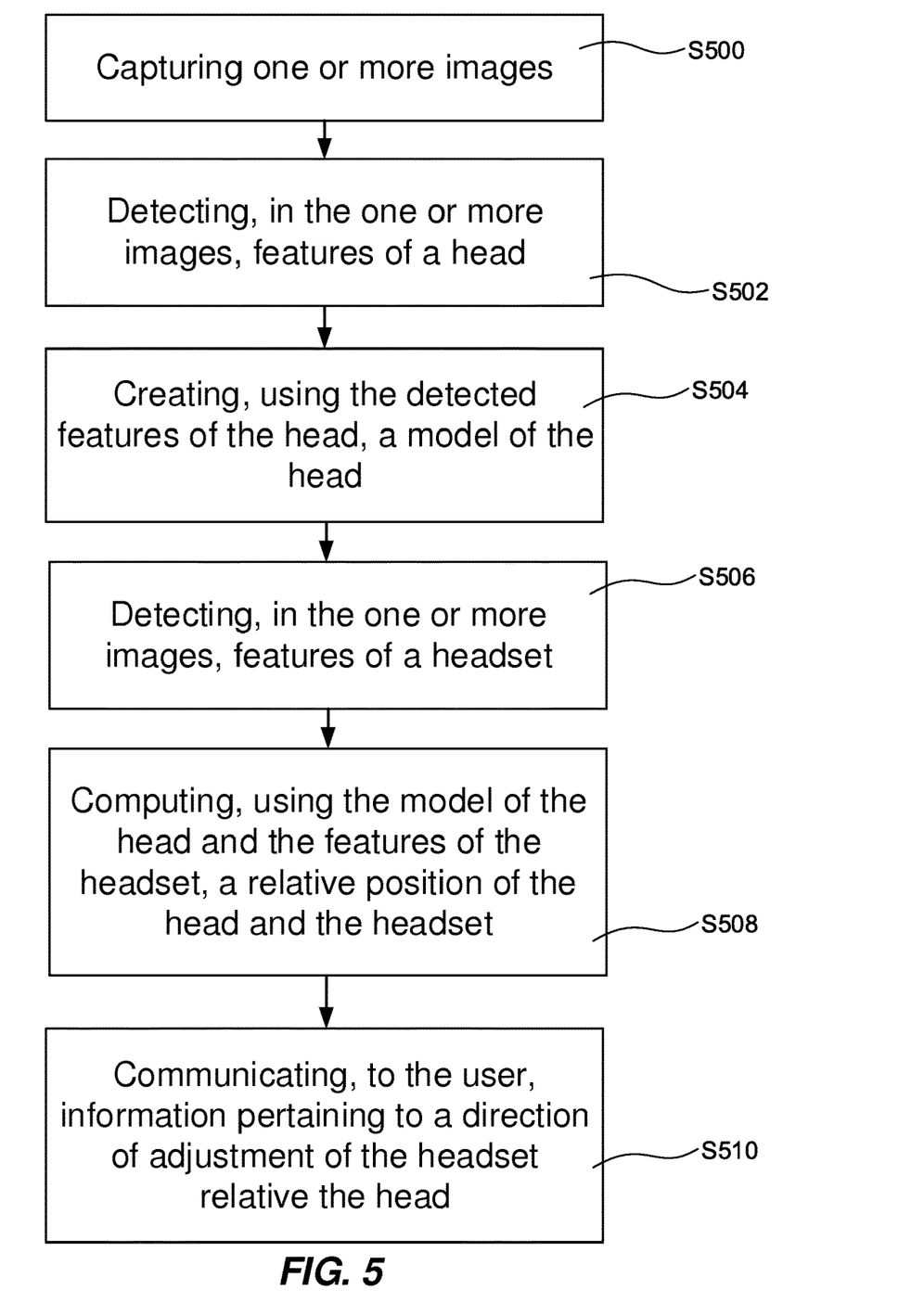
FIG. 5 is a block diagram of an alternative method of guiding positioning of the headset for transcranial brain stimulation on a head of a user of the headset.

With reference to FIG. 5 a method of guiding positioning of the headset 100 for transcranial brain stimulation on a head of a user of the headset 100 will be discussed. The method comprises one or more of the following acts. The acts may be performed in any order suitable.

Capturing S500 one or more headset images depicting the head of the user of the headset 100 wearing the headset 100. The capturing S500 may be made by a digital camera configured to capture still image. The capturing S500 may be made by a digital camera configured to capture video images. The camera may be a single image camera or a stereo camera. The one or more headset images may be a plurality of headset images.

Detecting S502, in the one or more headset images, features of the head. The features of the head may be eyes, mouth, nose, and/or face outline. The features may be detected using an active shape model or a neural network.

Creating S504, using the detected features of the head, a model of the head.

Detecting S506, in the one or more headset images, features of the headset 100. The features of the headset may e.g. comprise the electrodes 102A, 102B thereof.

Computing S508, using the model of the head and the features of the headset 100, a relative position of the head and the headset 100. The act of computing S508 may comprise comparing the created model of the head to a plurality of predetermined models of heads, wherein each predetermined model of a head comprises information pertaining to positioning of the headset 100 for that particular predetermined model of the head, and finding one predetermined model of a head being a best fit between the created model of the head and the plurality of predetermined models of heads.

In response to the relative position of the head and the headset 100 being above a threshold, computing, using the model of the head and the features of the headset, a direction of adjustment of the headset 100 relative the head. The direction of adjustment of the headset 100 relative the head may be in relative or direct terms. Hence, the user may be prompted to move the headset in a certain direction relative the head either by communicating in relative terms, e.g. move up the headset 100 upwards, downwards, to the left, to the right, etc., or by communicating in direct terms e.g. move up the headset 100 xcm upwards, ycm downwards, zcm to the left, kcm to the right, etc.

Communicating S510, to the user, information pertaining to the direction of adjustment of the headset 100 relative the head. The act of communicating S510, to the user, may be performed by displaying information on a display and/or announcing information via a loudspeaker. The display may be the display 153 of the electronic device 150 or a display of augmented reality glasses. The loudspeaker may be the loudspeaker 216 of the headset 100 or a loudspeaker 155 of the electronic device 150.

The act of communicating S510 may further comprise, in response to the relative position of the head and the headset 100 being at or below the threshold, communicating, to the user, information pertaining to that the headset is correctly positioned.

After a user has positioned the headset 100 on the head she may use the electronic device 150 to film or photograph her head. By detecting features of the head of the user a model of the head may be created. The model may be a 2D or 3D model depending on what kind of images are available from the electronic device 150. By detecting features of the headset a current positioning of the headset relative the head of the user may be found. After having created the model of the head of the user and finding the current positioning of the headset relative the head of the user, a correct position of the headset relative the head of the user may be overlayed on an image of the head of the user and verification if the headset is correctly positioned may be found. This will guide the user to position the headset, and especially the electrodes thereof, at the correct position relative the head of the user.

The person skilled in the art realizes that the present invention by no means is limited to the preferred embodiments described above. On the contrary, many modifications and variations are possible within the scope of the appended claims.

As described above, the headset comprises a wireless transceiver. This provides the possibility for the headset to communicate wirelessly with the electronic device over a network protocol such as Bluetooth or Wi-Fi. The skilled person understands that any network protocol capable of transmitting digitally represented data is possible to use.

The system may, through the electronic device, also provide the user with information about the transcranial brain stimulation progress such as logs of their use, changes to their schedule recommended by the physician, status of the headset regarding e.g. battery charge state or malfunctions, or any other information.

Further, the power source 202 of the headset 100 may be a chargeable battery. The headset may then comprise a charging port. The charging port may be located on an inside surface of the forehead frame 101. The inside surface of the forehead frame 101 being the surface of the forehead frame that is facing the forehead of the user upon use of the headset 100. This design will ensure that the headset cannot be charged upon usage of the same. This will enhance the safety of usage of the headset 100.

Further, A physician may use AR-glasses together with the above mentioned method of guiding positioning of a headset 100 for transcranial brain stimulation on a head of a user of the headset 100 in order to better position the headset 100 on the head of the user of the headset 100. For example, in the AR-glasses points corresponding to correct positioning of the electrodes may be displayed as an overlay on the head of the user.

As shown through this description, a headset, a kit and a system for transcranial brain stimulation is provided which allows a user to autonomously and conveniently perform steps of such treatment which previously required visits to or by a physician.

Additionally, variations to the disclosed embodiments can be understood and effected by the skilled person in practicing the claimed invention, from a study of the drawings, the disclosure, and the appended claims.

The invention claimed is:

1. A method of guiding positioning of electrodes for transcranial brain stimulation on a head of a user of the electrodes, the method comprising:
    capturing, using a camera, one or more head images depicting the head;
    detecting, in the one or more head images, features of the head;
    creating, using the detected features of the head, a model of the head;
    retrieving a plurality of predetermined models of heads subjected to transcranial brain stimulation;
    retrieving intended positions of the electrodes during transcranial brain stimulation for each of the plurality of predetermined models of heads that provides an optimal outcome from the transcranial brain stimulation;
    comparing the created model of the head to the plurality of predetermined models of heads;
    finding one predetermined model of a head being a best fit between the created model of the head and the plurality of predetermined models of heads; and
    displaying, on a display, a representation of the electrodes at intended positions associated with the one predetermined model as an overlay on an it age of the head of the user.

2. The method according to claim 1, further comprising:
    capturing one or more electrode images depicting the head of the user of the electrodes wearing the electrodes;
    detecting, in the one or more electrode images, features of the electrodes;
    computing, using the model of the head and the features of the electrodes, a relative position of the head and the electrodes;
    in response to the relative position of the head and the electrodes being above a threshold of deviation from the intended positions, computing, using the model of the head and the features of the electrodes, a direction of adjustment of the electrodes relative the head;
    communicating, to the user, information pertaining to the direction of adjustment of the electrodes relative the head.

3. The method according to claim 2, further comprising:
    in response to the relative position of the head and the electrodes being at or below the threshold, communicating, to the user, information pertaining to that the electrodes is correctly positioned.

4. The method according to claim 1, wherein the one or more electrode images is a subset of the one or more head images, or wherein the one or more electrode images is the same images as the one or more head images.

5. A non-transitory computer-readable recording medium having recorded thereon a program comprising program code portions which when executed on an electronic device having processing capabilities is configured to perform the method according to claim 1.

6. The method according to claim 1, wherein the electrodes are provided on a headset.

7. The method according to claim 1, wherein a position of at least one electrode is different between each of the plurality of predetermined models of heads.

8. A kit comprising:
- a headset for transcranial brain stimulation, the headset comprising a circuit comprising a first electrode, a second electrode; and
- a non-transitory computer-readable recording medium having recorded thereon a program which is executable on an electronic device having processing capabilities, wherein the program comprises program code portions which when executed on the electronic device is configured to:
  - receive one or more head images depicting a head of a user of the headset;
  - detect, in the one or more head images, features of the head;
  - create, using the detected features of the head, a model of the head;
  - retrieve a plurality of predetermined models of heads subjected to transcranial brain stimulation;
  - retrieve an intended position of the headset during transcranial brain stimulation for each of the plurality of predetermined models of heads that provides an optimal outcome from the transcranial brain stimulation for that predetermined model;
  - compare the created model of the head to the plurality of predetermined models of heads;
  - find one predetermined model of a head being a best fit between the created model of the head and the plurality of predetermined models of heads; and
  - display, on a display, a representation of the headset at the intended position associated with the one predetermined model as an overlay on an image of the head of the user.

9. The kit according to claim 8, wherein the program further comprises program code portions which when executed on the electronic device is configured to:
- receive one or more headset images depicting the head of the user of the headset wearing the headset;
- detect, in the one or more headset images, features of the headset;
- compute, using the model of the head and the features of the headset, a relative position of the head and the headset;
- in response to the relative position of the head and the headset being above a threshold of deviation from the intended position, compute, using the model of the head and the features of the headset, a direction of adjustment of the headset relative the head;
- communicate, to the user, information pertaining to the direction of adjustment of the headset relative the head.

10. The kit according to claim 9, wherein the program further comprises program code portions which when executed on the electronic device is configured to:
- in response to the relative position of the head and the headset being at or below the threshold, communicate, to the user, information pertaining to that the headset is correctly positioned.

11. The kit according to claim 9, wherein the communication, to the user, is performed by displaying information on a display and/or announcing information via a loudspeaker.

12. The kit according to claim 8, wherein the program further comprises program code portions which when executed on the electronic device is configured to:
- capture, using a camera of the electronic device, the one or more headset images and/or the one or more head images.

13. The kit according to claim 8,
wherein the headset further comprises:
- a wireless transceiver configured to wirelessly communicate with the electronic device;
- a power source configured to provide power to the circuit; and
- a controller being configured to control powering of the circuit according to a control signal, and wherein the program further comprises program code portions which when executed on the electronic device is configured to:
- retrieve a schedule for performing transcranial brain stimulation, and
- generate the control signal for the headset such that transcranial brain stimulation is performed according to the schedule for performing the transcranial brain stimulation.

14. The kit according to claim 8, wherein a position of the headset is different between each of the plurality of predetermined models of heads.

15. A non-transitory computer-readable recording medium having recorded thereon a program which is executable on an electronic device having processing capabilities, wherein the program comprises program code portions which when executed on the electronic device is configured to:
- receive one or more head images depicting a head of a user of electrodes for transcranial brain stimulation;
- detect, in the one or more head images, features of the head;
- create, using the detected features of the head, a model of the head;
- retrieve a plurality of predetermined models of heads subjected to transcranial brain stimulation;
- retrieve an intended position during transcranial brain stimulation for each of the plurality of predetermined models of heads that provides an optimal outcome from the transcranial brain stimulation for that predetermined model;
- compare the created model of the head to the plurality of predetermined models of heads;
- find one predetermined model of a head being a best fit between the created model of the head and the plurality of predetermined models of heads; and
- display, on a display, a representation of the electrodes at intended positions of the one predetermined model as an overlay on an image of the head of the user.

16. The non-transitory computer-readable recording medium according to claim 15, wherein a position of at least one electrode is different between each of the plurality of predetermined models of heads.

* * * * *

UNITED STATES PATENT AND TRADEMARK OFFICE
CERTIFICATE OF CORRECTION

| | |
|---|---|
| PATENT NO. | : 11,779,753 B2 |
| APPLICATION NO. | : 17/264308 |
| DATED | : October 10, 2023 |
| INVENTOR(S) | : Daniel Månsson et al. |

It is certified that error appears in the above-identified patent and that said Letters Patent is hereby corrected as shown below:

In the Claims

At Column 20, Claim number 1, Line number 37:
"model as an overlay on an it age of the head of the user."
Should read:
--model as an overlay on an image of the head of the user.--

Signed and Sealed this
Twenty-eighth Day of November, 2023

Katherine Kelly Vidal
*Director of the United States Patent and Trademark Office*